United States Patent [19]
Holland

[11] Patent Number: 4,887,597
[45] Date of Patent: Dec. 19, 1989

[54] NOSE PLUG

[76] Inventor: Bruce K. Holland, 2323 N. Woodlawn, #179, Wichita, Kans. 67220

[21] Appl. No.: 218,968

[22] Filed: Jul. 14, 1988

[51] Int. Cl.$^4$ .............................................. A61G 10/00
[52] U.S. Cl. .............................................. 128/206.11
[58] Field of Search .................... 128/206.11, 203.18, 128/201.18

[56] References Cited

U.S. PATENT DOCUMENTS

| | | | |
|---|---|---|---|
| 1,071,015 | 8/1913 | Adler | 128/206.11 |
| 2,097,846 | 11/1937 | Strauch | 128/206.11 |
| 2,241,472 | 5/1941 | Nemon | 128/206.11 |
| 2,282,681 | 5/1942 | Stotz | 128/206.11 |
| 2,660,166 | 11/1953 | Coleman | 128/206.11 |
| 3,463,149 | 8/1969 | Albu | 128/206.11 |
| 4,120,299 | 10/1978 | Russo | 128/206.11 |

FOREIGN PATENT DOCUMENTS 1231800  5/1971  United Kingdom .......... 128/206.11

Primary Examiner—David A. Wiecking
Assistant Examiner—Aaron J. Lewis
Attorney, Agent, or Firm—John W. Carpenter

[57] ABSTRACT

A nasal depository for absorbing mucus and the like from a person's nose. The nasal depository has at least one absorbent member for absorbing when contacted by nasal fluids. At least one hollow member is disposed through the absorbent members such that the hollow member has a pair of open ends that are unobstructed by the absorbent member. Such unobstruction allows the user to readily breathe. A perforated body member surrounds the absorbent member. A strap interconnects a pair of absorbent members such that each absorbent member is interconnected while lodging in the nasal passageway.

19 Claims, 1 Drawing Sheet

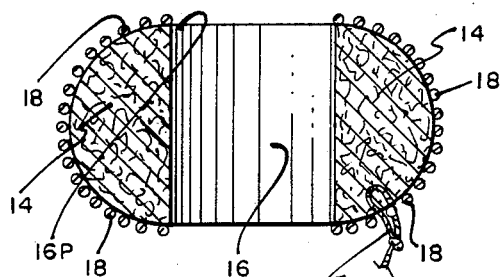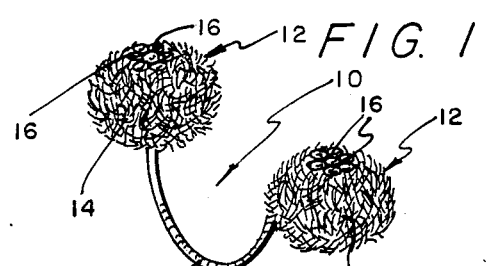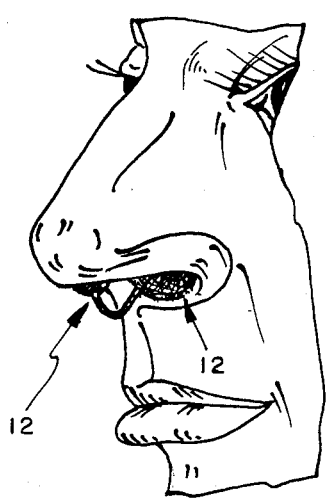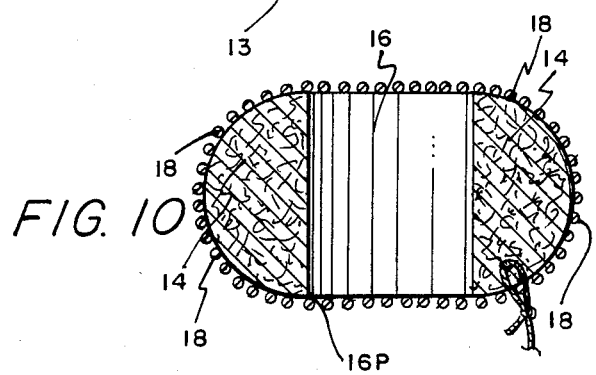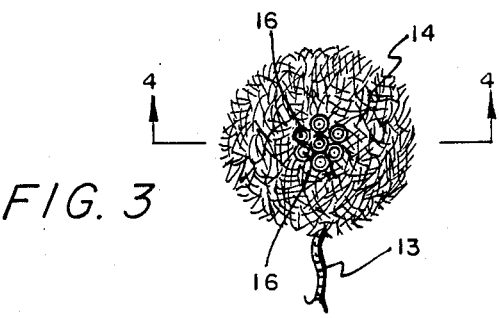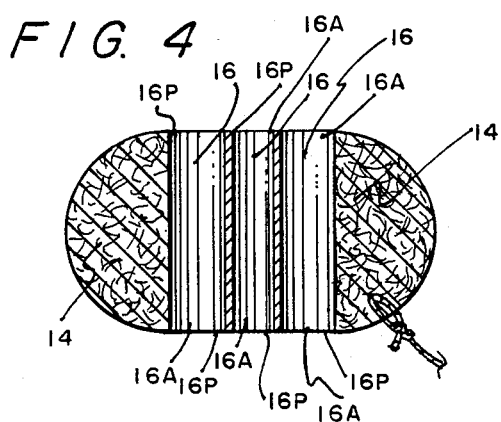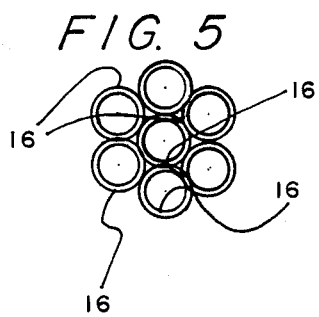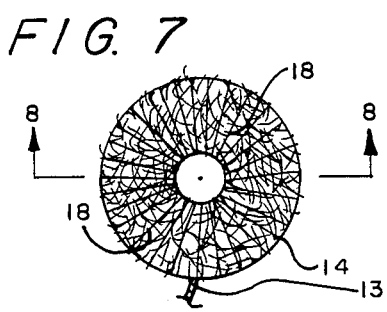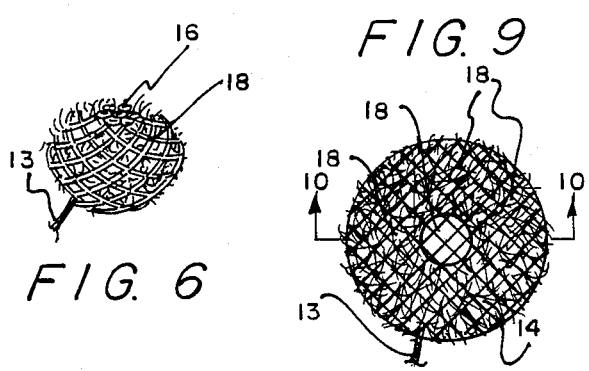

NOSE PLUG

BACKGROUND OF THE INVENTION

1. Field of the Invention

This invention is related to a nose plug. More specifically, this invention provides for a nasal depository for absorbing mucus and the like from the sinus passageways.

2. Description of the Prior Art

A patentability investigation was conducted and the following U.S. patents were discovered: U.S. Pat. No. 682,123 to Wilson; U.S. Pat. Nos. 701,538 and 758,030, both to Carence; U.S. Pat. No. 2,660,166 to Coleman; U.S. Pat. No. 2,890,695 to Safstrom; U.S. Pat. No. 4,120,299 to Russo; and U.S. Pat. No. 4,267,831 to Aguilar. None of the foregoing prior art teaches or suggests the particular nose plug of this invention.

SUMMARY OF THE INVENTION

The present invention accomplishes its desired objects by providing a nose plug, nasal depository, or the like for absorbing mucus and the like that emanates from sinus passageways. The nose plug or nasal depository comprises at least one absorbent means for absorbing fluids when contacted by the fluids; at least one hollow member with a pair of open ends extending through the absorbent means such that the open ends are unobstructed by the absorbent means; and a perforated body member surrounding the absorbent means and being supported by the same. The perforated body is preferably a net, a screen, or the like, and is formed of a material that retains its original shape when coming in contact with fluids that are being absorbed by the absorbent means. The absorbent means is preferably cotton. Preferably, there are a plurality of the hollow members that extend through the cotton.

The present invention also accomplishes its desired objects by providing a nasal depository that includes an assembly of nose plugs or depositories. More specifically, the nasal depository for absorbing mucus and the like comprises a first absorbent means and a second absorbent means, both for absorbing fluids when contacted by the same. A plurality of hollow members extend through both the first and second absorbent means. A first perforated body surrounds the first absorbent means and is supported by the same; and a second perforated body member surrounds the second absorbent means and is supported by the same. A strap means interconnects the first absorbent means with the second absorbent means.

It is therefore an object of the present invention to provide a nose plug or nasal depository.

This object, together with the various ancillary objects and features which will become apparent to those skilled in the art as the following description proceeds, is attained by this novel nasal depository, a preferred embodiment being shown with reference to the accompanying drawings, by way of example only, wherein:

BRIEF DESCRIPTION OF THE DRAWINGS

FIG. 1 is a perspective view of the nasal depository of this invention;

FIG. 2 is a perspective view of the nasal depository being inserted into the nasal passageway of a user;

FIG. 3 is a top plan view of one of the absorbing elements of the nasal depository;

FIG. 4 is a vertical sectional view taken in direction of the arrows and along the plane of line 4—4 in FIG. 3;

Fig. 5 is a top plan view of a plurality of the hollow members which extend through one or both of the absorbent means that constitute the nasal depository of this invention;

FIG. 6 is a side elevational view of one of the absorbent means of the nasal depository having a perforated body or net surrounding the absorbent means;

FIG. 7 is a top plan view of another embodiment of one of the absorbent means having a single hollow conduit extending therethrough with the perforated body or net secured around the perimeter of the hollow conduit and surrounding the absorbent member of the absorbing means;

FIG. 8 is a vertical sectional view taken in direction of the arrows and along the plane of line 8—8 in FIG. 7;

FIG. 9 is a top plan view of another embodiment of one of the absorbent means having a single hollow cylindrical member and with the perforated body or net completely encapsulating or surrounding the absorbent member in the hollow cylindrical member that extends through the absorbent member of the absorbent means; and FIG. 10 is a vertical sectional view taken in direction of the arrows and along the plane of line 10—10 in FIG. 9.

DETAILED DESCRIPTION OF THE INVENTION

Referring in detail now to the drawings, wherein similar part of the invention are identified by like reference numerals, there is seen the nose plug, nasal depository, or the like, of this invention, generally identified as 10. The nasal depository 10 preferably comprises a pair of absorbing means, each generally identified as 12. The pair of absorbing means 12—12 are interconnected by a strap 13.

Each absorbing means 12 comprises an absorbent member 14 (e.g. cotton, etc.) that is formed such as to be easily inserted into a nasal passageway. Extending through the absorbent member 14 is one or more hollow cylindrical members 16 which function to allow the user of nasal depository 10 to easily breath when the nostrils contain the nasal depository 10. Hollow cylindrical members 16 allow outside air to be withdrawn therethrough and carbon dioxide emanating from the lungs to be discharged thereout. Each hollow member 16 has an opening 16a surrounded or circumscribed by a perimetrical body structure 16p. In a preferred embodiment of the invention, a perforated body 18, which is preferably a net, screen, or the like, surrounds the absorbent member 14. The perforated body 18 is supported by the absorbent member 16 but should be formed of material (e.g. nylon, soft plastics, etc.) that is rigid enough to retain or maintain its original shape, when coming in contact with fluids that are being absorbed by the absorbent member 14. Typically the absorbent member 14 shrinks when absorbing sinus fluids and if the perforated body 18 also shrank, the absorbing means 12—12 would easily become dislodged from the nostrils. Thus, if the perforated body 18 is initially formed or shaped to snugly engage the surfaces of the nasal passageways or nostrils, shrinkage of the absorbent member 14 would not affect the engagement of the perforated body 18 with the surfaces of the nasal passageways. Stated alternatively, as the absorbent member 14 shrinks, the perforated body 18 maintains its original geometric form even upon contact with nasal fluids, and the nasal depository remains within the nasal passageway of the user.

The perforated body 18 may be situated around the absorbent member 14 in a number of fashions. The perforated body as depicted in FIG. 6 may be merely disposed around the absorbent member 14 without being in contact or connected to any hollow member 16, and without covering any of the openings 16a of any hollow member 16. The perforated body 18 may also be secured to at least one of the perimetrical body structures 16p of any hollow member 16 as disclosed in FIGS. 7 and 8. Alternatively, the perforated body 18 may completely cover at least one of the openings 16a of one or more hollow members 16, as depicted in FIGS. 9 and 10. Thus, the openings 16a of any hollow member may or may not be unobstructed. The strap member 13 may be engaged 20 directly to absorbent members 14—14, or strap 13 may be engaged to each of the perforated body 18 that respectively surrounds the pair of absorbent members 14—14 that performs the absorbing functions of the nasal depository 10 of this invention.

While the nasal depository 10 has been depicted as comprising a pair of absorbing means 12—12, it is to be understood that a single absorbing means is within the spirit and scope of the present invention. Such single absorbing means may be employed in the circumstances or situations where there would be need for only a single absorbing means, such as blood or mucus originating through only one nasal passageway on one side of a user's nose.

While the present invention has been described herein with reference to particular embodiments thereof, a latitude of modification, various changes and substitutions are intended in the foregoing disclosure, and it will be appreciated that in some instances some features of the invention will be employed without a corresponding use of other features without departing from the scope of the invention as set forth.

I claim:

1. A nasal depository for absorbing mucus and the like comprising at least one absorbent means for absorbing fluids when contacted by the fluids; at least one hollow member formed from a material different than the material of said absorbent means with a pair of open ends extending through the absorbent means such that the open ends are unobstructed by the abosrbent means; and a perforated body member surrounding said absorbent means and being supported by the same.

2. The nasal depository of claim 1 wherein said perforated body member generally borders both of the open ends of the hollow member.

3. The nasal depository of claim 2 wherein said open ends of the hollow member define a first opening circumscribed by a first perimetrical body structure and a second opening circumscribed by a second perimetrical body structure.

4. The nasal depository of claim 3 wherein said perforated body member is secured to said first perimetrical body structure and to said second perimetrical body structure such as to unobstruct said first opening and said second opening.

5. The nasal depository of claim 1 wherein said perforated body member extends over at least one of the open ends of said hollow member.

6. The nasal depository of claim 4 wherein said perforated body is formed of a material that retains its original shape when coming in contact with fluids that are being absorbed by the absorbent means.

7. The nasal depository of claim 5 wherein said perforated body is formed of a material that retains its original shape when coming in contact with fluids that are being absorbed by the absorbent means.

8. A nasal depository for absorbing mucus and the like comprising a first absorbent means and a second absorbent means, both for absorbing fluids when contacted by the fluids; a plurality of first hollow members formed from a material different than the material of said absorbent means, each with a pair of first open ends and extending through the first absorbent means such that the first open ends are unobstructed by the first absorbent means; a plurality of second hollow members, each with a pair of second open ends and extending through the second absorbent means such that the second open ends are unobstructed by the second absorbent means; a first perforated body member surrounding said first absorbent means and being supported by the same; a second perforated body member surrounding said second absorbent means and being supported by the same; and a strap means connected to said first absorbent means and to said second absorbent means.

9. The nasal depository of claim 1 wherein said absorbent means is cotton.

10. The nasal depository of claim 9 wherein said perforated body member is a net.

11. The nasal depository of claim 10 wherein said hollow member defines a hollow cylindrical tubular body.

12. The nasal depository of claim 8 wherein said first perforated body member extends over at least one of the first open ends of said first hollow members.

13. The nasal depository of claim 8 wherein said second perforated body member extends over at least one of the second open ends of said second hollow members.

14. The nasal depository of claim 8 wherein said first perforated body is formed of a material that retains its original shape when coming in contact with fluids that are being absorbed by the absorbent means.

15. The nasal depository of claim 8 wherein said second perforated body is formed of a material that retains its original shape when coming in contact with fluids that are being absorbed by the absorbent means.

16. The nasal depository of claim 8 wherein said first and second absorbent means is cotton.

17. The nasal depository of claim 16 wherein said first and second perforated body member is a net.

18. The nasal depository of claim 17 wherein said first and second hollow members define a hollow cylindrical tubular body.

19. A nasal depository for absorbing mucus and the like comprising at least one absorbent means for absorbing fluids when contacted by the fluids; at least one hollow member formed from a material different than the material of said absorbent means with a pair of open ends extending through the absorbent means such that the open ends are unobstructed by the absorbent means; and a perforated body member surrounding said absorbent means and being supported by the same;

said open ends of the hollow member define a first opening circumscribed by a first perimetrical body structure and a second opening circumscribed by a second perimetrical body structure; and said perforated body member is secured to said first perimetrical body structure and to said second perimetrical body structure such as to unobstruct said first opening and said second opening.

* * * * *